United States Patent [19]

Itoigawa et al.

[11] Patent Number: 5,755,668
[45] Date of Patent: May 26, 1998

[54] CATHETER HAVING PRESSURE DETECTING ABILITY

[75] Inventors: Koichi Itoigawa; Hitoshi Iwata, both of Aichi, Japan

[73] Assignee: Kabushiki Kaisha Tokai Rika Denki Seisakusho, Aichi-Ken, Japan

[21] Appl. No.: 774,967

[22] Filed: Dec. 26, 1996

[30] Foreign Application Priority Data

Jan. 9, 1996 [JP] Japan .................................... 8-001799

[51] Int. Cl.$^6$ ................................................ A61B 5/02
[52] U.S. Cl. ............................ 600/488; 600/485; 600/561
[58] Field of Search .................................. 600/485, 488, 600/561

[56] References Cited

U.S. PATENT DOCUMENTS 4,722,648  2/1988  Ligtenberg .
4,809,704  3/1989  Sogawa .
5,178,153  1/1993  Einzig .
5,526,820  6/1996  Khoury .
5,564,425  10/1996  Tonokura .

Primary Examiner—Jennifer Bahr
Assistant Examiner—Roy Gibson
Attorney, Agent, or Firm—Quarles & Brady

[57] ABSTRACT

A catheter provided with a catheter tube that is inserted into a human body. A sensor detects pressure acting on a distal end of the catheter tube when inserted into the human body and outputs an output signal indicating fluctuations of the pressure. A CPU judges whether the waveform of the output signal contains a regular component and an irregular component and separates the output signal into a regular component and an irregular component based on the judgment. Based on the separated irregular component, a judgment is made as to whether an obstruction is present within an insertion path of the catheter.

13 Claims, 5 Drawing Sheets

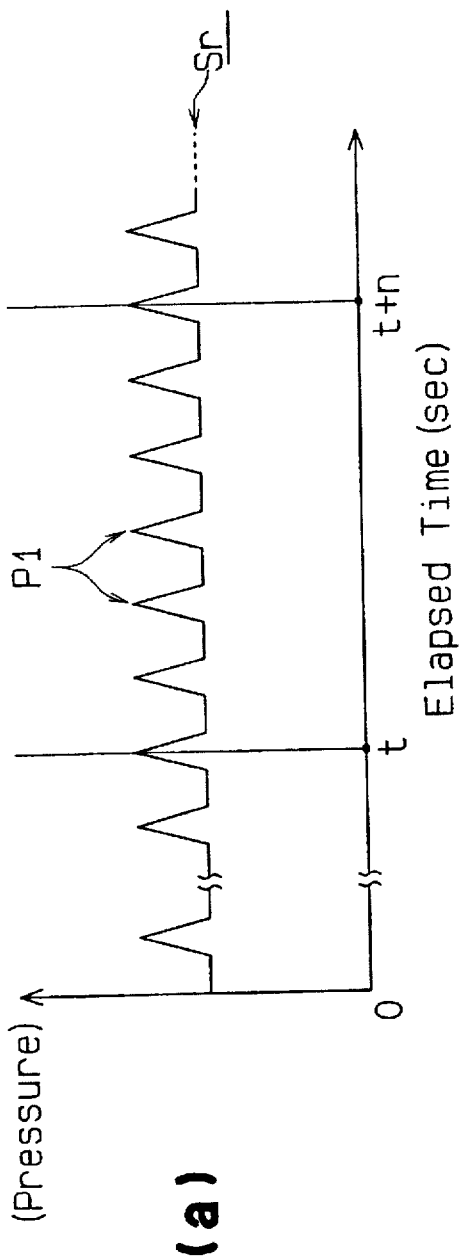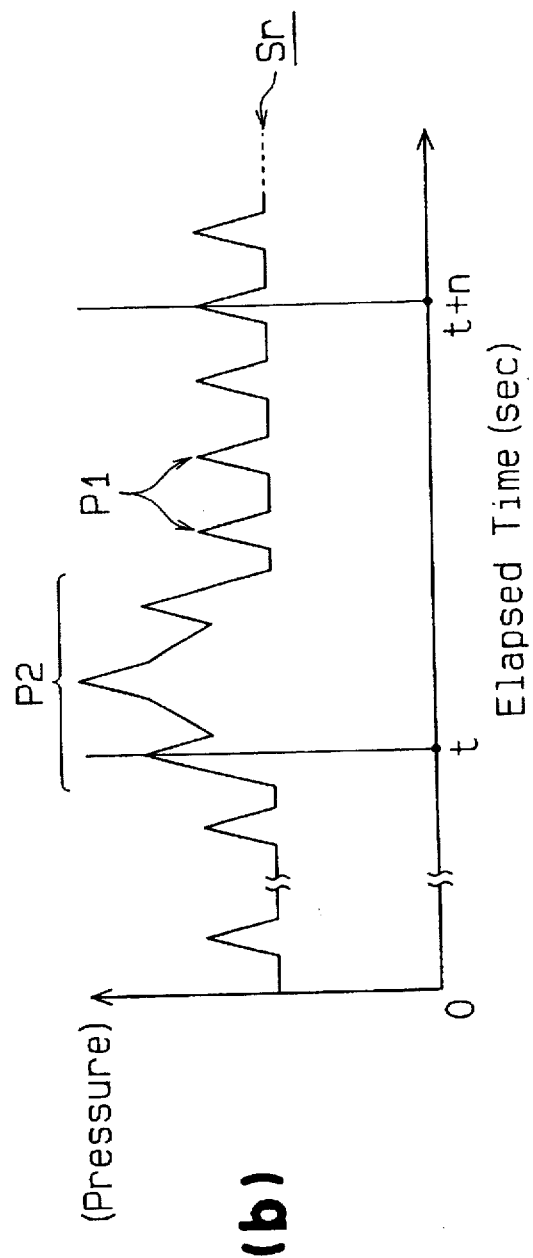
Fig.2 (a)    Fig.2 (b)

5,755,668

CATHETER HAVING PRESSURE DETECTING ABILITY

BACKGROUND OF THE INVENTION

1. Field of the Invention

The present invention relates to a catheter, and more particularly, to a catheter that detects pressure applied to the distal end of the catheter when inserted into the human body.

2. Description of the Related Art

Catheters are a type of medical instrument insertable into the human body. Catheter tubes, which constitute catheters, have diameters of approximately 1 mm to 9 mm and are inserted into various vessels within the human body, one being a blood vessel. The distal end of the catheter tube is guided into a desired position of the body to carry out medical treatments such as measurements of blood pressure and expansion of blood vessels at this position. Thus, the operator of the catheter must accurately guide the distal end of the catheter tube to the desired position by means of external operations.

The vessels within the human body often bend and branch off in different directions and are not necessarily straight. Furthermore, the diameter of the tubes are not always uniform but are naturally very small or have become small due to obstructions including blood clots existing within the vessels.

However, with a conventional catheter that is not provided with a means to detect the forward travel direction of the catheter tube, the operator must rely on his own feeling to operate the catheter tube. Hence, skill is necessary to guide the distal end of the catheter tube to the desired position.

In order to eliminate this problem, it has recently been proposed to provide sensors on the distal end of the catheter tube for detecting obstructions and operating the catheter tube based on the sensing result.

Conventional catheters provided with obstruction sensing sensors have, for example, a structure described below. A chip retaining chamber is partitioned by walls in the distal portion of a catheter tube. A semiconductor pressure sensor chip equipped with a distortion gauge is stored within the chip retaining chamber and is mounted to a substrate. Moreover, a silicon gel, which functions as a pressure transmitting medium, fills the inside of the chip retaining chamber. An opening of the catheter tube is sealed by an elastic cap.

Therefore, if pressure is applied to the outer surface of the catheter, the pressure is transferred to the sensor chip through the silicon gel generating a variation in the electrical resistance value of the sensor chip. As a result, the sensor outputs a signal S externally in response to the variations of the pressure (refer to FIG. 5). By monitoring the fluctuations of this signal S, the operator may sense the presence of an obstruction.

However, when a catheter having the above structure is inserted into a blood vessel, the following problems occur. Blood is always circulating through the blood vessels and the pressure of the blood fluctuates as time elapses. Consequently, components of the output signal S not only include fluctuation caused by contact with obstructions but also include fluctuation caused by blood pressure. The fluctuation caused by blood pressure appears regularly as a small pulse in the graph of FIG. 5. Therefore, with a catheter having such structure, accurate sensing of the existence of an obstruction may be hindered, depending on the situation.

The present invention addresses the above-mentioned problems. The object of the present invention is to provide a catheter provided with a sensor that is capable of accurately sensing the state of the forward travel direction.

SUMMARY OF THE INVENTION

The catheter according to the present invention is provided with a catheter tube that is inserted into a human body. A detecting means detects pressure acting on a distal end of the catheter tube when inserted into the human body and outputs an output signal indicating fluctuations of the pressure. A separating means judges whether a waveform of the output signal contains a regular component and an irregular component and separates the output signal into the regular component and the irregular component based on the judgement. Based on the separated irregular component, a judgment is made on whether an obstruction is present within an insertion path of the catheter.

The present invention provides a method for detecting an obstruction within a vessel of a human body by means of detecting the pressure applied to a tube inserted into the vessel. The method judges whether a regular component and an irregular component are contained in an output signal sent from a detecting means provided on a distal end of the tube when inserting the tube. The output signal is separated into a regular component and an irregular component based on the judgment. An obstruction existing within the vessel is displayed based on the separated irregular component.

BRIEF DESCRIPTION OF THE DRAWINGS

The features of the present invention that are believed to be novel are set forth with particularity in the appended claims. The invention, together with objects and advantages thereof, may best be understood by reference to the following description of the presently preferred embodiments together with the accompanying drawings in which:

FIG. 2(a) is a graph showing the waveform of an output signal of the sensor when there is no obstruction in the forward travel direction of the catheter;

FIG. 2(b) is a graph showing the waveform of the output signal of the sensor when there is an obstruction;

DETAILED DESCRIPTION OF THE PREFERRED EMBODIMENTS

Figure 1:
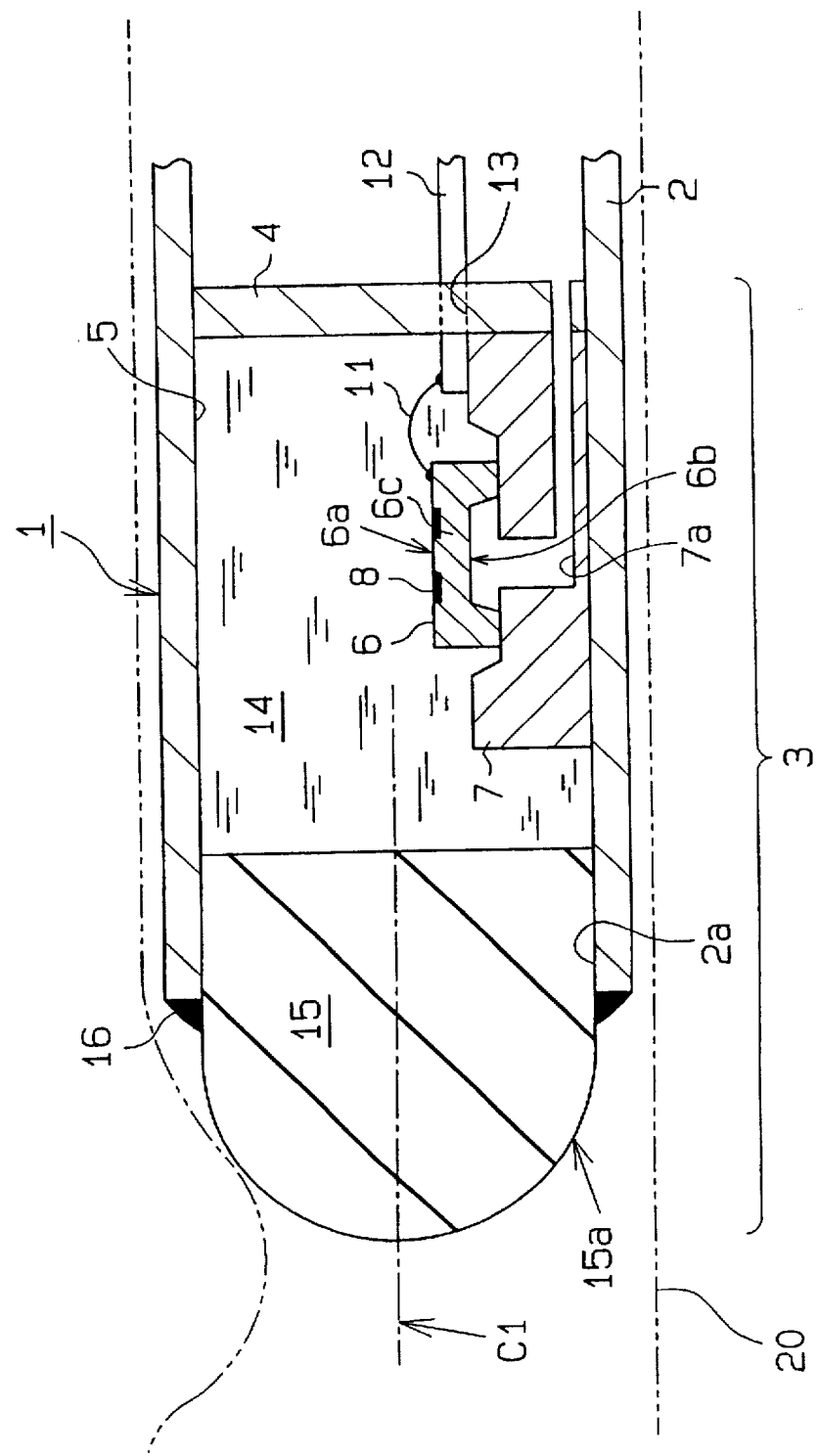
FIG. 1 is a schematic cross-sectional view showing a distal portion of a catheter provided with a sensor according to an embodiment of the present invention.

A blood vessel catheter 1 according to a first embodiment of the present invention will now be described with reference to FIGS. 1 to 4.

The blood vessel catheter 1 is provided with a catheter tube 2 inserted into a blood vessel 20 and a main body apparatus (shown schematically in FIG. 3) located at a basal end of the tube to operate the catheter tube externally. The catheter tube 2 constitutes a portion of a catheter and is a flexible tube-shaped member that is inserted into the human body. The main body apparatus includes a control device, a microcomputer 21 and a display device 26.

The control device is provided with, for example, a plurality of wires inserted inside the tube 2 and a wire control portion to control the wires. Further, an air compressor (not shown in figure) is arranged at the basal end of the tube 2 to inflate an expansion balloon provided near the distal end of the tube 2. An air supplying tube (not shown) is connected to the compressor. The air supplying pipe is inserted through the tube 2 and the distal end of the pipe is connected to the distal end of the balloon. Air is supplied to expand the balloon and expand the constricted blood vessel 20 from the inner side.

A sensor portion 3 is defined at the distal end of the catheter tube 2 in the catheter 1 of this embodiment. An opening 2a in the distal end of the catheter tube 2 is sealed by a cap 15 and a seal 16, which function as a sealing member. The seal 16 is elastic and ring-shaped. In addition to sealing the gap between the cap 15 and the opening 2a, the seal allows fine movement along the axis C1 by the cap 15.

A partition 4 is provided in the distal end of the tube 2. The cap 15 and the partition 4 define a chip retaining chamber 5 for the sensor portion 3. A semiconductor pressure sensor chip 6 is retained within the chip retaining chamber 5 mounted to a substrate 7. Both the sensor chip 6 and the substrate 7 are flat and have a substantially rectangular cross section. The long sides of the sensor chip 6 and the substrate 7 are arranged along the axis C1 and the short sides (not shown) of the sensor chip 6 and the substrate 7 are arranged perpendicular to the axis C1. The length of the short side of the substrate 7 is slightly less than the inside diameter of the tube 2 and the length of the long side of the substrate 7 is somewhat greater than the inside diameter of the tube 2.

The sensor chip 6 has a thin-wall portion 6c defined at its center. A plurality of distortion gauges 8 are formed on the upper surface of the thin-wall portion 6c, namely, on pressure sensitive surface 6a. Therefore, in this embodiment, the pressure sensitive surface 6a extends in a direction perpendicular to the axis C1. A pad is provided on the upper surface of the sensor chip 6 and the upper surface of the substrate 7. The pads of the sensor chip 6 and the substrate 7 are joined to each other by a bonding wire 11. Further, a lead wire of a signal cable 12 is joined to the pad of the substrate 7. The signal cable 12 passes through a through-hole 13 of the partition 4 and extends through the tube 2 reaching the basal end of the catheter.

A communicating hole 7a is defined in the substrate 7 and a cavity 6b is provided on the side opposite to the pressure sensitive surface 6a of the sensor chip 6. The communicating hole 7a connects the internal region of the catheter at the basal side of the partition 4 to the cavity 6b. Therefore, back pressure, or namely, atmospheric pressure, acts on the sensor chip 6 as a reference pressure. Furthermore, the space between the inner wall of the tube 2 and the substrate 7 in the chip storage chamber 5 is filled with a silicon gel 14 that functions as a pressure transmitting medium.

The catheter 1 of this embodiment is inserted into a blood vessel from the cap 15 at its distal end. Therefore, the pressure inside the blood vessel initially acts on the outer surface of the cap 15 or, in other words, the pressure receiving surface 15a. For the material of the cap 15, biocompatible resin material such as polytetrafluoroethylene (PTFE) or vinyl chloride is used.

When there is an obstruction or a constricting portion such as a blood clot or a tumor inside the blood vessel 20, in which the tube 2 is inserted, the insertion resistance against the tube 2 increases when the distal end of the sensor 3, namely, the pressure receiving surface 15a of the cap 15, is pressed against the obstruction or the constricting portion. This increases the pressure acting on the pressure receiving surface 15a of the cap 15 and finely moves the cap 15 toward the sensor chip 6.

As a result, the pressure applied to the silicon gel 14 inside the chip retaining chamber 5 increases the pressure applied to the pressure sensitive surface 6a. In other words, pressure fluctuations occurring outside the sensor 3 are indirectly transmitted to the pressure sensitive surface 6a through the silicon gel 14.

This increases distortions of the pressure sensitive surface 6a and generates variations in the electrical resistance value of the distortion gauges 8. Therefore, the sensor chip 6 outputs a signal in response to variations in the resistance value of the distortion gauges 8, that is, an analog signal Sr is output externally in response to variations in the pressure applied to the catheter.

The output signal Sr is input to the microcomputer 21 arranged at the basal end of the chip 2 through the bonding wire 11 and the signal cable 12. The output signal Sr is sent to the display device 26 after undergoing predetermined processing carried out by the microcomputer 21. The fluctuations of the pressure are then displayed by the display device 26.

The procedures for signal processing in the catheter 1 of this embodiment will now be described referring to FIGS. 2 to 4. When an obstruction does not exist in the forward travel direction of the catheter 1, the sensor chip 6 outputs the output signal Sr having a waveform as shown in FIG. 2(a). Only the fluctuating component of the blood pressure is contained in the output signal Sr. The waveform of the output signal Sr has a certain regularity. Small pulses P1 having substantially identical forms within the output signal Sr correspond to the beating of the heart, namely, the variations in the pulsations of the blood pressure.

The regularity of the output signal Sr is fundamentally based on the regularity in the variations in the pulsation of the blood pressure itself. The peaks of the small pulses P1 correspond to the highest blood pressure value and the bottoms correspond to the lowest blood pressure value.

In contrast, when an obstruction exists in the forward travel direction of the catheter 1, the sensor chip 6 outputs an output signal Sr having a waveform containing a large pulse P2, as shown in FIG. 2(b). The fluctuating component of the pressure due to contact with the obstruction is contained in this output signal Sr in addition to the fluctuating component due to blood pressure pulsations. The large pulse P2 in this output signal Sr corresponds to the fluctuating component of the pressure due to contact with the obstruction. This type of waveform component is different from the fluctuating component due to blood pressure pulsation and does not have regularity.

Figure 3:
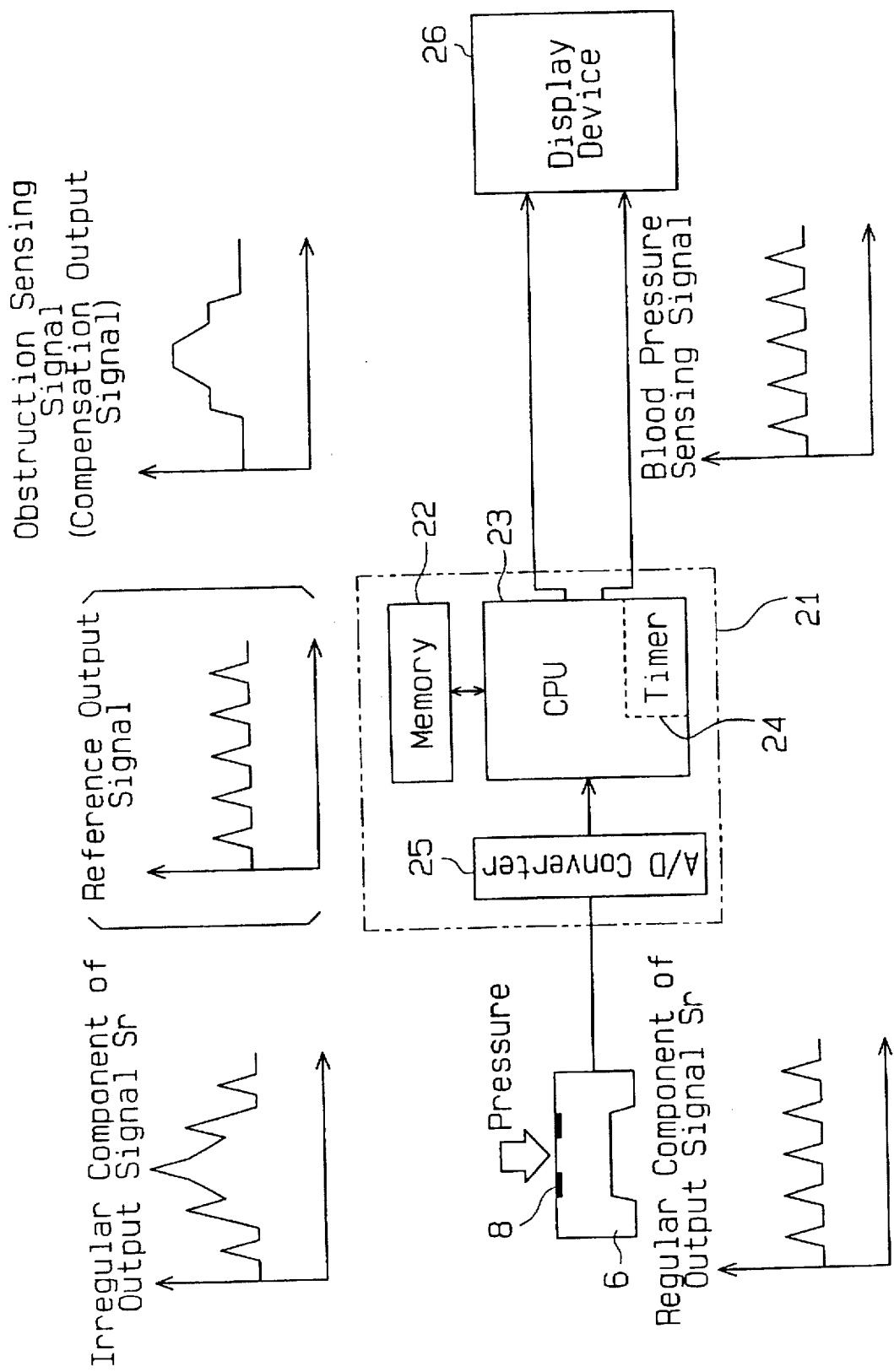
FIG. 3 is a diagrammatic drawing explaining a signal processing procedure carried out by the catheter.

As diagrammatically shown in FIG. 3, the analog output signal Sr from the sensor chip 6 is gradually input to the microcomputer 21, which serves as a separating means. The microcomputer 21 includes a memory 22, a CPU 23, a timer 24, and an analog/digital (A/D) converter 25.

After the A/D converter digitizes the analog output signal of the sensor chip 6, the signal is output to the CPU 23. The memory 22 temporarily stores the input digital output signal Sr.

In brief, the CPU 23 reads two output signals Sr, Ss from the memory 22 with a predetermined time interval between each reading. The CPU 23 compares the signals Sr, Ss and obtains the difference ΔS through computations. The output signal Sr is t seconds before the present and the output signal Ss is t+n seconds before the present. At this moment, output signal Ss is considered to be a reference signal used for computations.

Alphabetic t represents a predetermined positive number. Alphabetic n represents a numeric value calculated from the number of heartbeats at that moment, or the period (seconds) of the pulsation. As the value of t is set smaller, sensing delay of the sensor becomes smaller. In this embodiment, the value of t is set from approximately 100 msec. to approximately 700 msec. and preferably, from approximately 400 msec. to approximately 700 msec. Further, each time is measured by the timer 24 inside the CPU 23.

The CPU 23 constantly outputs a blood pressure sensing signal externally. When an obstruction is detected, the CPU 23 externally outputs the obtained difference ΔS as a compensation output signal, or an obstruction sensing signal Sm.

Figure 4:
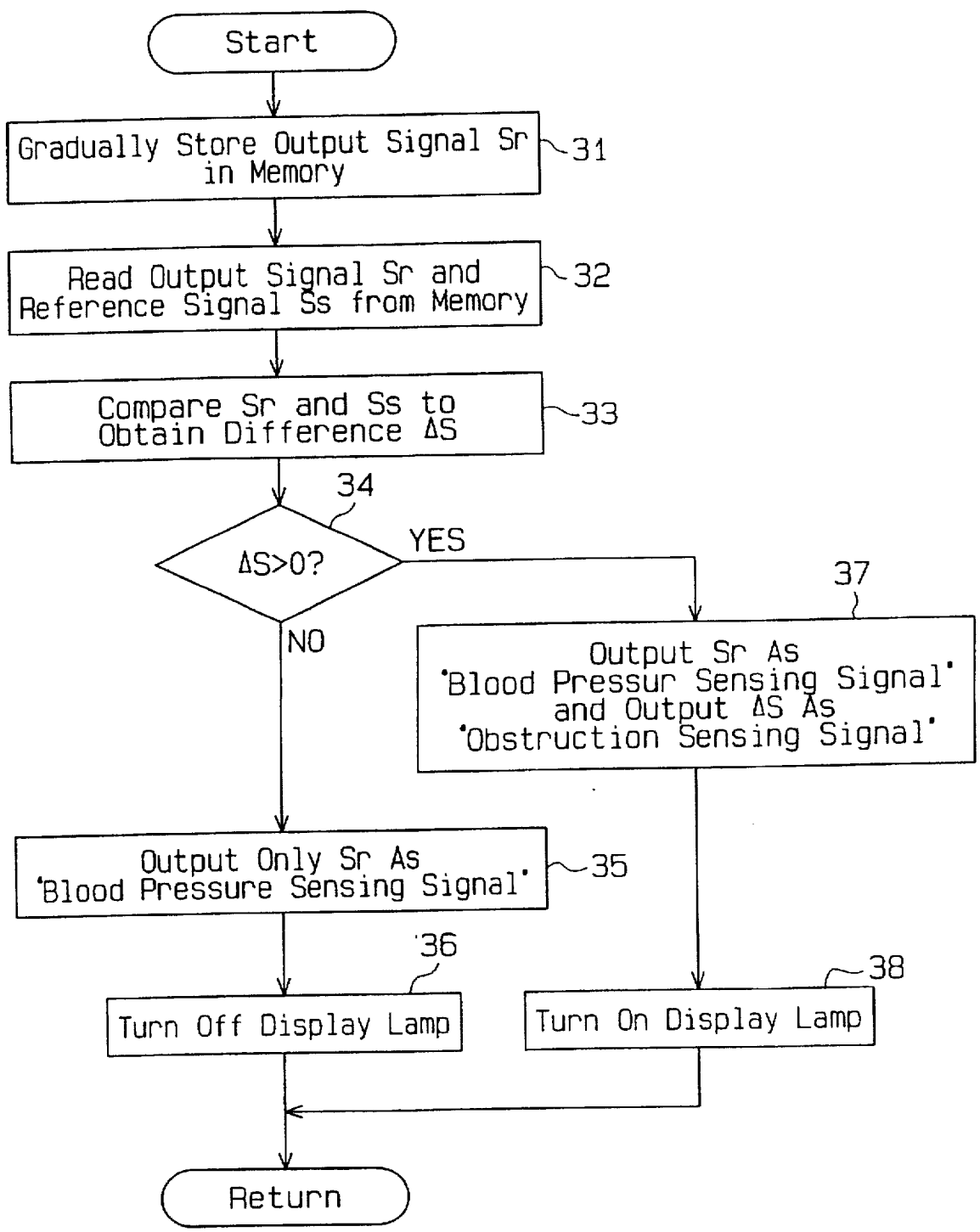
FIG. 4 is a flowchart explaining the signal processing procedure carried out by the catheter.
Figure 5:
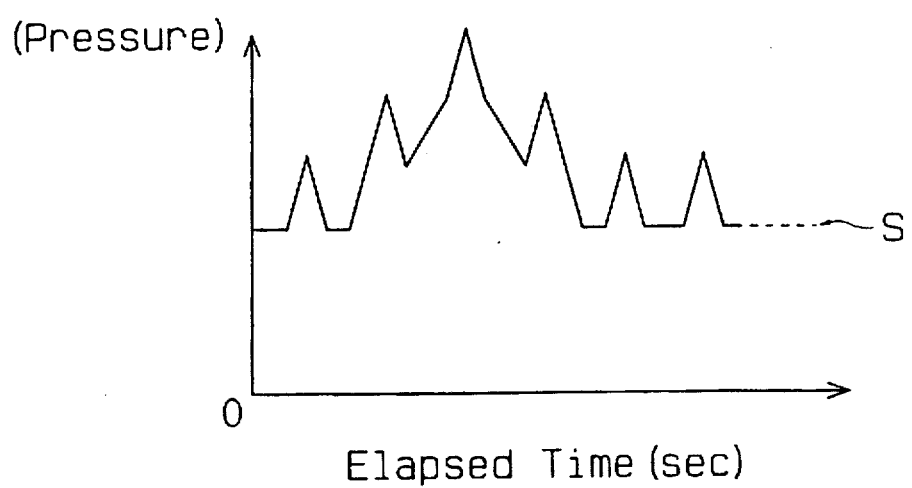
FIG. 5 is a graph showing the waveform of an output signal of the prior art sensor provided in a catheter.

To process signals, in step 31 of FIG. 4, the CPU 23 inputs the continuous output signal Sr from the sensor chip 6 through the A/D converter 25 and then temporarily stores the signal Sr in the memory 22. The following description will be made under the assumption that the prior output signals Sr are stored in the memory 22. Furthermore, among the output signals Sr stored in the memory 22, for example, the data that has been stored for t+n seconds or more is either deleted or renewed in step 31. After step 31, the CPU 23 proceeds to the next step 32.

In step 32, the CPU 23 reads the output signal Sr t seconds before and the reference signal Ss t+n seconds before from the memory 22. Thereafter, the CPU 23 proceeds to the next step 33. In step 33, the CPU 23 compares both signals Sr and Ss and obtains the difference ΔS therebetween. Thereafter, the CPU 23 proceeds to the next step 34.

In step 34, the CPU 23 judges whether the value of difference ΔS obtained beforehand is a positive value. When the judgment result corresponds to difference ΔS≦0, that is, when there is no obstruction in the blood vessel, the CPU 23 proceeds to the next step 35. Conversely, when the result corresponds to ΔS>0, that is, when there is an obstruction in the blood vessel, the CPU 23 does not proceed to the next step 35 but proceeds to another step 37.

In step 35, the CPU 23 solely outputs the output signal Sr as a "blood pressure sensing signal" to the display device 26. A calculator installed in the display device 26 obtains the blood pressure and the number of heartbeats based on the output signal Sr and displays the result on the screen using symbols such as numerals. Thereafter, the CPU 23 proceeds to the next step 36.

In step 36, the CPU 23 maintains the display lamp displaying "obstruction exists" in the screen of the display device 26 at an OFF state. Thereafter, the CPU 23 returns to the initial step 31 and begins the same processing.

As described above, when there is a difference ΔS≦0, the operator of the catheter 1 can find out if there is an obstruction in the forward travel direction of the catheter by monitoring the display device 26. This enables the operator to judge whether to continue the pressing operation of the catheter 1.

When the judgment of step 34 concludes that the difference ΔS>0, in step 37, the CPU 23 not only outputs the output signal Sr as a "blood pressure sensing signal" but also outputs the difference ΔS as a "compensation output signal Sm, namely, obstruction sensing signal Sm". Based on the result, the calculator of the display device 26 obtains the blood pressure and the number of heartbeats and displays the result on the screen using symbols such as numerals. Thereafter, the CPU 23 proceeds to the next step 38.

In step 38, the CPU 23 maintains the display lamp displaying "obstruction exists" in the screen of the display device 26 at an ON state. Thereafter, the CPU 23 returns to the initial step 31 and begins the same processing. The display lamp indicating "obstruction exists" may be flashed to further precaution the operator. In addition to lighting or flashing the display lamp of "obstruction exists", the pressure received from the obstruction may be computed based on the obstruction sensing signal Sm to indicate the pressure on the screen using numerals. Furthermore, in addition to the "obstruction exists" message, other messages including "constriction exists" or "caution" may also be displayed.

As described above, when a difference ΔS>0 is determined, the operator of the catheter 1 monitors the display device 26 to grasp the existence of an obstruction in the forward travel direction. This enables the operator to determine not to continue the pressing operation of the catheter 1. For this case, measures can be devised including changing the travel path of the catheter 1 to a different path by operating the wires. Furthermore, when a judgment is made that the obstruction is a constriction or a blood clot, medical treatment for the obstruction may be directed and measurement operations such as blood pressure measurements may be carried out.

This embodiment employs the microcomputer 21 to process signals. This separates the output signal Sr into a component P1 having regularity in the fluctuations of the waveform and a component P2 that does not have regularity. Therefore, it is possible to separate only the objective component P2, or the fluctuating component caused by contact with the obstruction. Moreover, even if the fluctuating component caused by the blood pressure acts on the sensor chip 6, this does not affect the sensing result. Therefore, the sensing accuracy is improved in comparison to a device not employing this type of signal processing. The operator may accurately detect the state of the forward travel direction based on an accurate sensing result. Accordingly, the distal end of the catheter tube 2 may accurately be guided to a desired position within the blood vessel 20.

The difference ΔS between the output signal Ss and the output signal Sr corresponds to the fluctuating component of the detection pressure caused by contact between the catheter 1 and the obstruction. Thus, the fluctuating component caused by the blood pressure is eliminated from the output signal Sr and only the fluctuating component caused by contact between the obstruction is displayed as the compensation output signal Sm. This processing is possible since both the output signal Sr and the reference signal Ss contain component P1, which has regularity in the waveform fluctuations. By obtaining the difference ΔS, the components P1 offset each other, which allows the component P2, which does not have regularity in the waveform, to be obtained.

In this embodiment, the above processing is executed by the microcomputer 21. This improves the separation properties of waveform components P1, P2 in comparison to the same processing through an analog circuit. Accordingly, even if the level of the two waveform components P1, P2 contained within output signal Sr are close to each other, the components P1, P2 may be positively separated. This improves the sensing accuracy in comparison to an analog circuit.

The present invention is not restricted to the above embodiment and may be modified as described below.

In step 34 of FIG. 4, the judgment reference value may be set at a positive number (x) in place of "0". When, for example, ΔS≦x is satisfied, the processing proceeds to step 35 and when ΔS>x is satisfied, the processing proceeds to step 37. For this case, even if there is a little unevenness of the value of the difference ΔS, this may be tolerated. However, it is preferable for x to be a small numeric value.

In step 38 of FIG. 4, instead of lighting and flashing the display lamp, or in addition to lighting and flashing the display lamp, an auditory alarm may be sounded. In step 32 of FIG. 4, the reference output signal Sr is obtained by successively accessing output signal Sr during time t. In place of this, for example, the reference output signal Ss may be stored into memory 22 in advance and constantly be used. Further, a separate blood pressure sensor may be provided at a location other than the sensor 3 of the catheter tube 2. The difference ΔS may be obtained by using the output signal from the separate blood pressure sensor. However, an embodiment with a simple structure employing only one semiconductor pressure sensor chip 6 is more preferable than such a two-sensor modification.

The waveform components included in the output signal Sr may consist of three or more types of waveform components. Instead of processing the digital signal with the microcomputer 21, for example, an analog circuit may be used to process the signals. The signal output from the sensor 6 is not restricted to an electronic signal but may also be an optical signal.

The present invention may also be applied to a catheter 1 having a sensor portion that differs from the sensor portion 3 employed in the above embodiment. For example, in place of the cap 15 and the seal 16, a simple sealing plug made of silicon rubber may be used. Further, the invention is not restricted to a relative pressure type sensor as in the above embodiment. The present invention may be applied to a catheter provided with an absolute pressure type sensor. The catheter 1 according to the present invention may be inserted into vessels other than the blood vessel 20 in the human body. For example, the catheter 1 may be inserted into the bronchial tube, the digestive tube, the lymphatic vessel or the urethra.

What is claimed is:

1. A catheter comprising:

a catheter tube adapted for insertion into a human body;

a detection means that detects pressure acting on a distal end of said catheter tube when inserted into the human body, said detecting means outputting an output signal indicating fluctuations of the pressure;

a separating means for judging whether a waveform of the output signal contains a regular component (P1) and an irregular component (P2), said separating means separating the output signal into the regular component and the irregular component based on the judgement.

2. The catheter according to claim 1 further comprising a display device for displaying at least the irregular component of the two components separated by said separating means.

3. The catheter according to claim 1, wherein said separating means includes a memory means for storing the output signal and a reference signal, which is compared with the output signal, said separating means computing a difference between the output signal and the reference output signal to separate the output signal into a regular component and an irregular component.

4. The catheter according to claim 3, wherein said reference signal is selected from the output signals sent from said detection means.

5. The catheter according to claim 1, wherein said detection means includes:

a retaining chamber defined at a distal end of said catheter tube;

a sensor chip disposed within said retaining chamber, said sensor chip outputting a signal in response to pressure applied to the sensor chip; and a transmitting medium filling said retaining chamber for transmitting the pressure applied to the distal end of the catheter to the sensor chip.

6. The catheter according to claim 5 wherein said separating means includes:

a converter that performs analog/digital conversion of the output signal sent from said sensor chip;

a memory that stores the output signal converted by said converter after a predetermined time interval;

a central processing unit (CPU) that reads two output signals converted by said converter and obtains a difference between the two signals.

7. The catheter according to claim 6, wherein said CPU judges whether an obstruction is present within an insertion path of said catheter tube in accordance with the difference obtained by the CPU.

8. The catheter as stated in claim 7 further comprising a display device, said display device displaying the judgement result of whether an obstruction is present within the insertion path of said catheter tube.

9. A catheter comprising:

a hollow catheter tube adapted for insertion into a blood vessel of a human body;

a cap for closing a distal end of said catheter tube;

a partition for defining a retaining chamber in the distal end of said catheter in cooperation with said cap;

a sensor accommodated within said retaining chamber, said sensor outputting a signal corresponding to the pressure applied to the sensor when said catheter tube is inserted into the blood vessel;

a transmitting medium filling said retaining chamber for transmitting the pressure applied to the cap of the catheter to said sensor;

a separating means for judging whether a waveform of the output signal contains a regular component (P1) and an irregular component (P2), said separating means separating the output signal into the regular component and the irregular component based on the judgement.

10. The catheter according to claim 9, wherein said separating means includes:

a converter that performs analog/digital conversion of the output signal sent from said sensor chip;

a memory that stores the output signal converted by said converter after a predetermined time interval;

a central processing unit (CPU) that reads two output signals converted by said converter and obtains a difference between the two signals.

11. The catheter according to claim 10, wherein said CPU judges whether an obstruction is present within an insertion path of said catheter tube in accordance with the difference obtained by the CPU.

12. The catheter according to claim 11 further comprising a display device, said display device displaying the judgement result of whether an obstruction is present within the insertion path of said catheter tube.

13. A method for detecting an obstruction within a vessel of a human body by means of detecting the pressure applied to a tube inserted into the vessel, said method comprising the steps of:

inserting a tube into a blood vessel and detecting pressure applied to the tube judging whether a regular component (P1) and an irregular component (P2) are contained in an output signal sent from a detecting means provided on a distal end of the tube when inserting the tube;

separating said output signal into a regular component and an irregular component based on said judgment;

displaying an obstruction existing within said vessel based on the separated irregular component.

* * * * *